United States Patent [19]

Moore

[11] 4,179,441
[45] Dec. 18, 1979

[54] FUNGIDAL AND HERBICIDAL 2-SUBSTITUTED-3-OXA-3Aλ⁴, 4-DITHIA-6-HALO-1,5-DIAZAPENTALENE

[75] Inventor: Joseph E. Moore, Richmond, Calif.

[73] Assignee: Chevron Research Company, San Francisco, Calif.

[21] Appl. No.: 866,122

[22] Filed: Dec. 30, 1977

[51] Int. Cl.$^2$ .................................. C07D 277/20
[52] U.S. Cl. .............................. 548/122; 424/270; 71/90
[58] Field of Search .......... 260/302 F, 302 R, 306.8 F

[56] References Cited
U.S. PATENT DOCUMENTS
3,726,891  4/1973  Pilgram et al. ............... 260/302 F

*Primary Examiner*—Nicholas S. Rizzo
*Attorney, Agent, or Firm*—D. A. Newell; T. G. DeJonghe; Lawrence S. Squires

[57] ABSTRACT

Herbicidal and fungicidal oxadithiadiazapentalenes of the formula

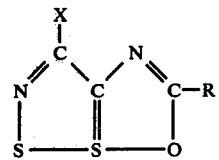

wherein X is halo and R is alkyl, haloalkyl, halovinyl, cycloalkyl, thiocayanatoalkyl, aryl, aryloxy, arylthiomethyl, aryloxymethyl, benzylthiomethyl, benzyloxymethyl or heterocyclic are prepared by reacting a sulfur halide and an N-cyanomethylcarboxamide of the formula

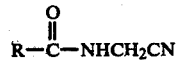

wherein R is as defined above.

10 Claims, No Drawings

FUNGIDAL AND HERBICIDAL 2-SUBSTITUTED-3-OXA-3A$\lambda^4$, 4-DITHIA-6-HALO-1,5-DIAZAPENTALENE

BACKGROUND OF THE INVENTION

The following publications disclose azapentalenes and thiapentalenes of a variety of structures: (1) D. H. Reid et al, JCS 775 (1975); (2) R. M. Christie et al, JCS 848 (1977); (3) C. Th. Pedersen, JCS 994 (1977); (4) D. H. Reid et al, JCS 2097 (1975); (5) R. H. Reid et al, JCS 854 (1977) and (6) G. L'Abbe et al, Angew. Chem. Int. Ed. Engl. 16 (1977) No. 6.

DESCRIPTION OF THE INVENTION

The oxadithiadiazapentalene compounds of the invention are represented by the formula (I)

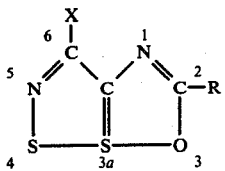

wherein X is chloro, bromo or iodo and R is alkyl of 1 to 6 carbon atoms; haloalkyl of 1 to 6 carbon atoms and of 1 to 3 of the same or different halogen selected from fluoro, chloro, bromo or iodo; halovinyl of 1 to 3 of the same or different halogens selected from fluoro, chloro, bromo or iodo; cycloalkyl of 3 to 6 carbon atoms; thiocyanatoalkyl of 1 to 3 carbon atoms; phenyl or phenoxy substituted with up to 3 (0 to 3), preferably up to 2 (0 to 2), of the same or different substituents selected from hydroxy, fluoro, chloro, bromo, iodo, trifluoromethyl, trichloromethyl, tribromomethyl, alkyl of 1 to 4 carbon atoms, alkoxy of 1 to 4 carbon atoms, alkoxycarbonylalkoxy of 3 to 6 carbon atoms, nitro, cyano, thiocyanato or isothiocyanato; phenoxymethyl or phenylthiomethyl wherein the phenyl ring is substituted with up to 3 (0 to 3), preferably up to 2 (0 to 2), of the same or different substituents selected from fluoro, chloro, bromo, iodo or alkyl of 1 to 4 carbon atoms; benzyloxymethyl or benzylthiomethyl wherein the benzyl ring is substituted with up to 2 of the same or different substituents selected from fluoro, chloro, bromo, iodo or alkyl of 1 to 4 carbon atoms; furyl; or thienyl.

Representative alkyl R groups include methyl, ethyl, isopropyl, t-butyl, and hexyl. Representative haloalkyl R groups include fluoromethyl, dichloromethyl, tribromomethyl, 1-chloroethyl, 2-iodoethyl, pentachloroethyl, 3-bromopropyl, 2-iodo-4-fluorobutyl and 2,4-dichlorohexyl. Representative halovinyl R groups include 2-chlorovinyl, 1,2-dibromovinyl and trifluorovinyl. Representative cycloalkyl R groups include cyclopropyl, cyclobutyl, cyclopentyl and cyclohexyl. Representative thiocyanatoalkyl R groups are thiocyanatomethyl and 3-thiocyanatopropyl. Representative substituted-phenyl and phenoxy R groups include 4-hydroxy-2-methylphenyl, 2,4-difluorophenyl, 4-bromophenyl, 2,4,6-trichlorophenyl, 4-trifluoromethylphenyl, 3,5-dimethylphenyl, 3-methoxyphenoxy, 3-(methoxycarbonylmethoxy)phenoxy, 2,4-dinitrophenoxy, 4-cyanophenyl and 4-isothiocyanatophenyl. Representative substituted phenoxymethyl and phenylthiomethyl R groups include 4-chlorophenoxymethyl, 2,4-dibromophenoxymethyl, 4-methylphenoxymethyl, 3,4-dimethylphenylthiomethyl and 2-methyl-4-iodophenylthiomethyl. Representative substituted benzyloxymethyl and benzylthiomethyl R groups include 3,5-difluorobenzyloxymethyl, 3-bromobenzyloxymethyl, 4-iodobenzyloxymethyl, 2,4-dichlorobenzylthiomethyl and 3,5-dimethylbenzylthiomethyl.

A preferred class of oxadithiadiazapentalene compounds is that wherein X is chloro, bromo or iodo and R is phenyl substituted with up to 2 (0 to 2) of the same or different substituents selected from hydroxy, fluoro, chloro, bromo, nitro, iodo, alkyl of 1 to 4 carbon atoms, trifluoromethyl or trichloromethyl.

Another preferred class of oxadithiadiazapentalene compounds is that wherein X is chloro, bromo or iodo and R is phenoxymethyl, phenylthiomethyl, benzyloxymethyl or benzylthiomethyl wherein the aromatic ring is substituted with up to 2 (0 to 2) of the same or different substituents selected from fluoro, chloro, bromo, iodo or alkyl of 1 to 4 carbon atoms. In this class, R preferably is phenoxymethyl substituted with up to 2 of the same or different substituents selected from fluoro, chloro, bromo, iodo or alkyl of 1 to 4 carbon atoms.

The most preferred class of oxadithiadiazapentalene compounds is that wherein X is chloro, bromo or iodo, preferably chloro, and R is haloalkyl of 1 to 6 carbon atoms, preferably 1 to 3 carbon atoms, and of 1 to 3 of the same or different halogens selected from fluoro, chloro or bromo or iodo. The most preferred compounds of this class are those wherein R is monohalomethyl wherein the halo is chloro, bromo or iodo.

Representative compounds of the invention include:
2-methyl-3-oxa-3a$\lambda^4$,4-dithia-6-chloro-1,5-diazapentalene
2-(2-chloroethyl)-3-oxa-3a$\lambda^4$,4-dithia-6-chloro-1,5-diazapentalene
2-tribromovinyl-3-oxa-3a$\lambda^4$,4-dithia-6-chloro-1,5-diazapentalene
2-(2-thiocyanatoethyl)-3-oxa-3a$\lambda^4$,4-dithia-6-chloro-1,5-diazapentalene
2-(2-hydroxy-4-bromophenyl)-3-oxa-3a$\lambda^4$,4-dithia-6-chloro-1,5-diazapentalene
2-(4-trichloromethylphenyl)-3-oxa-3a$\lambda^4$,4-dithia-6-chloro-1,5-diazapentalene
2-(4-cyanophenyl)-3-oxa-3a$\lambda^4$,4-dithia-6-chloro-1,5-diazapentalene
2-(3-iodophenoxy)-3-oxa-3a$\lambda^4$,4-dithia-6-chloro-1,5-diazapentalene
2-cyclopropyl-3-oxa-3a$\lambda^4$,4-dithia-6-iodo-1,5-diazapentalene
2-(2,4-dinitrophenyl)-3-oxa-3a$\lambda^4$,4-dithia-6-bromo-1,5-diazapentalene
2-(4-methoxyphenyl)-3-oxa-3a$\lambda^4$,4-dithia-6-chloro-1,5-diazapentalene
2-(phenoxymethyl)-3-oxa-3a$\lambda^4$,4-dithia-6-bromo-1,5-diazapentalene
2-(3-iodophenylthiomethyl)-3-oxa-3a$\lambda^4$,4-dithia-6-chloro-1,5-diazapentalene
2-(4-methylbenzylthiomethyl)-3-oxa-3a$\lambda^4$,4-dithia-6-chloro-1,5-diazapentalene
2-(4-chlorobenzylmethyl)-3-oxa-3a$\lambda^4$,4-dithia-6-chloro-1,5-diazapentalene
2-(3-furyl)-3-oxa-3a$\lambda^4$,4dithia-6-bromo-1,5-diazapentalene
2-(2-thienyl)-3-oxa-3a$\lambda^4$,4-dithia-6-bromo-1,5-diazapentalene The oxadithiadiazapentalene compounds are produced by reacting a sulfur halide e.g., a sulfur dihalide such as sulfur dichloride or a sulfur monohalide such as sulfur monochloride, and an N-cyanomethyl carboxamide represented by the formula (II):

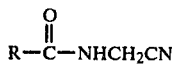
(II)

wherein R has the same significance as previously defined. The N-cyanomethyl carboxamide (II) is generally prepared by reacting an acid chloride RCOCl wherein R is as defined above and a cyanomethylamine by conventional procedures.

The precise mechanism and the reaction intermediates involved in the reaction of the sulfur halide and the carboxamide (II) are not known with certainty. However, it is known that the stoichiometry of the reaction is at least about two mols of sulfur halide per mol of carboxamide. Therefore, suitable molar ratios of carboxamide to sulfur halide are about 1:2 to 1:8, although molar ratios of about 1:2 to 1:5 are preferred. The preferred sulfur halide reactant is a sulfur dihalide, especially sulfur dichloride.

Preferably, reaction (I) is conducted in the presence of catalytic amount of a guaternary ammonium salt. Generally, amounts of quaternary ammonium salt per mol of sulfur halide vary from about 0.01 to 0.3, although amounts from 0.05 to 0.2 mols per mol of sulfur halide are preferred. Suitable quaternary ammonium salts are tetralkylammonium halides wherein the alkyl has 1 to 6 carbon atoms and the halide is fluoro, chloro, bromo or iodo, e.g., tetramethylammonium chloride or tetrabutylammonium bromide. When a quaternary salt is employed as a catalyst, the anion is preferably the same halide as the halide of the sulfur halide reactant.

In general, the reaction is accomplished by reacting the carboxamide (II), the sulfur halide and the quaternary salt catalyst in an inert liquid organic diluent. Suitable inert diluents include alkanes and haloalkanes, such as hexane, isooctane, or dichloromethane; aromatic compounds, such as benzene, toluene, chlorobenzene; oxygenated hydrocarbon such as acyclic alkyl ethers, such as dimethoxyethane and dibutyl ether; and cyclic ethers such as dioxane, tetrahydrofuran and tetrahydropyran. Generally, the amount of diluent employed ranges from 1 to 50 mols per mol of sulfur halide.

The reaction is suitably conducted at a temperature of 0° C. to the boiling point of the diluent, although temperatures between 0° C. and 100° C. are preferred. Generally, the reactants are contacted at ambient temperature or lower, e.g., about 0° C. to 25° C., and the reaction is completed at elevated temperatures, e.g., about 25° to 100° C. The reaction is conducted at or above atmosphere pressure. The reaction time will, of course, vary depending on the reaction temperature and the particular reactants employed. Generally, however, the reaction time varies from ½ hour to 24 hours. The progress of the reaction can sometimes be determined by the evolution of hydrogen halide gas from the reaction mixture and the completion of the reaction can sometimes be determined by the cessation of gas evolution. The oxadithiadiazapentalene product is isolated from the reaction mixture by conventional procedures, e.g., extraction, chromatography, crystallization, etc.

Compounds of the invention having a substituted methyl group at the two position of the ring can be also prepared by reacting a oxadithiadiazapentalene of the formula

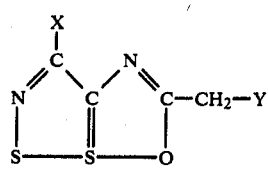
(III)

wherein Y is chloro, bromo or iodo, with the appropriate nucleophilic reactant. For example, the compound wherein R is iodomethyl can be prepared by reacting the corresponding chloromethyl compound with sodium iodide; the compound wherein R is thiocyanatomethyl can be prepared from a compound of formula (III) and ammonium thiocyanate; and compounds wherein R is phenoxymethyl, phenylthiomethyl, benzyloxymethyl or benzylthiomethyl can be prepared by reacting an appropriate oxide or mercaptide salt (e.g., sodium phenoxide or benzyl mercaptide) with a compound of formula (III).

The compounds of formula (I) wherein R is iodomethyl or thiocyanatomethyl are preferably prepared from a compound of formula (III).

EXAMPLE 1

Preparation of 2-(3,4-dichlorophenyl-3-oxa-3aλ⁴,4-dithia-6-chloro-1,5-diazapentalene A solution of 24 g (0.23 mol) triethylamine in 50 ml dichloromethane was added dropwise over about 40 minutes to a stirred mixture of 10.7 g (0.1 mol) aminoacetonitrile hydrochloride and 20.9 (0.1 mol) 3,4-dichlorobenzoyl chloride. The reaction mixture become warm and the hydrochloride almost completely dissolved. The reaction mixture was washed with water, thereby causing the separation of a solid. The solid was filtered, washed with water and dried to give 9.3 g of a white solid. A 1.0 g sample of the solid was recrystallized from 50 ml benzene to give 0.7 g of N-cyanomethyl-3,4-dichlorobenzamide, m.p. 144°–145° C. Elemental analysis for $C_9H_6Cl_2N_2O$ showed: %Cl, calc. 30.9, found 31.1.

A solution of 5.4 g (0.023 mol) N-cyanomethyl-3,4-dichlorobenzamide, 10 g (0.09 mol) sulfur dichloride, 1 g tetrabutylammonium chloride and 300 ml dichloromethane was stirred at about 25° C. Gases were evolved during the reaction. After stirring for 75 minutes, thin-layer chromatography did not show any of the unreacted benzamide. The reaction mixture was evaporated under reduced pressure to give a red solid. The solid was chromatographed on silica gel (benzene eluant) to give 4.3 g of a yellow solid, melting point 144°–160° C. Two recrystallizations from hexane/benzene raised the melting point to 170°–172° C. The infrared spectrum of the product showed strong adsorption at 6.2 micron. Elemental analysis for the product is tabulated in Table I, as Compound No. 1.

EXAMPLE 2

Preparation of 2-chloromethyl-3-oxa-3aλ⁴,4-dithia-6-chloro-1,5-diazapentalene

A 153-g (1.4 mol) sample of sulfur dichloride was added slowly over a two-hour period to a mixture of 65.8 g (0.49 mol) N-cyanomethyl-alpha-chloroacetamide and 2 g tetrabutylammonium chloride in 500 ml dichloromethane. The reaction mixture was stirred at about 250° C. for 4 hours and filtered to give 76 g of a yellow solid. The solid was refluxed in toluene until solution occurred and stripped to give 50.7 g of product, m.p. 120°–122° C. The infrared spectrum of the product showed strong adsorption at 6.3 micron. Elemental analysis for a recrystallized sample melting at 122°–124° C. is tabulated in Table I, as Compound No. 5.

EXAMPLE 3

Preparation of 2-iodomethyl-3-oxa-3a$\lambda^4$,4-dithia-6-chloro-1,5-diazapentalene A mixture of 7 g (0.033 mol) 2-chloromethyl-3-oxa-3a$\lambda^4$,4-dithia-6-chloro-1,5-diazapentalene and 10.0 g (0.066 mol) sodium iodide in 100 ml acetone was stirred for 1 hour at about 25° C. The reaction mixture was filtered to remove solids formed during the reaction. The filtrate was evaporated under reduced pressures and the residue was crystallized from benzene/hexane to give 5.5 g of the product as an orange solid, m.p. 107°–108° C. Elemental analysis for the product is tabulated in Table I as Compound No. 9.

EXAMPLE 4

Preparation of 2-(2-furyl)-3-oxa-3a$\lambda^4$,4-dithia-6-chloro-1,5-diazapentalene A 20.2-g (0.2 mol) sample of triethylamine was added dropwise over 20 minutes to a stirred and cooled (ice bath) mixture of 9.3 g (0.1 mol) aminoacetonitrile hydrochloride in 150 ml chloroform. A solution of 13.2 g (0.1 mol) 2-furoyl chloride in 25 ml dichloromethane was then added dropwise over 20 minutes. The ice bath was removed and the reaction mixture stirred for 25 minutes. The reaction mixture was then washed with water, dried over magnesium sulfate and evaporated to give 7.4 g of crude N-cyanomethyl-2-furamide, as a beige solid, m.p. 85°–93° C. Recrystallization from benzene gave the furamide as a white solid, m.p. 101°–102° C. Elemental analysis for $C_7H_6N_2O$ showed: %C, calc. 56.0, found 56.0; %H, calc. 4.06, found 4.11; %N, calc. 18.7, found 19.1.

A solution of 17 g (0.15 mol) sulfur dichloride in 25 ml dichloromethane was added dropwise over 20 minutes to a solution of 6.3 g (0.4 mol) N-cyanomethyl-2-furamide and 0.5 g tetrabutylammonium chloride in 100 ml dichloromethane. Gases were evolved from the resulting cherry-red reaction mixture. The reaction mixture was then stirred for 2 hours at about 25° C., during which time solids separated. The solids were filtered and heated under reflux in 25 ml toluene until gas evolution ceased. On cooling, 3.5 g of 6-chloro-2-(2-furyl), as a yellow solid melting at 126°–133° C., was obtained. The infrared spectrum of the product showed strong adsorption at 6.2 micron. Elemental analysis for the product is tabulated in Table I, as Compound No. 8.

EXAMPLE 5

Preparation of 2-(4-chlorophenylthio-methyl)-3-oxa-3a$\lambda^4$,4-dithia-6-chloro-1,5-diazapentalene A solution of 0.1 mol sodium p-chlorophenylmercaptide was prepared by reacting at about 0° C., 14.5 g (0.1 mol) p-chlorophenylmercaptan and 2.4 g (0.1 mol) sodium hydride in 150 ml dimethylformamide. To the solution cooled to 0° C. was then added in small portions 13.2 g (0.1 mol) N-cyanomethyl-alpha-chloroacetamide. The reaction was stirred for 1 hour at 25° C. and poured into 500 ml ice water. The reaction mixture was then filtered to give a solid. The solid was dissolved in dichloromethane and the resulting solution was dried over magnesium sulfate and evaporated to give 18.7 g of N-cyanomethyl-alpha-(p-chlorophenylthio)acetamide, as a white solid which melted at 89°–91° C. after recrystallization from hexane/benzene.

A mixture of 8.0 g (0.033 mol) of N-cyanomethyl-alpha-(p-chlorophenylthio) acetamide, 0.5 g tetrabutylammonium chloride and 14 g (0.135 mol) sulfur dichloride in 150 ml dichloromethane was stirred at about 25° C. for 1 hour. Gases were evolved and solids formed. The solids were filtered and heated in 75 ml toluene until gas evolution ceased and a homogeneous solution was obtained. The solution was evaporated under reduced pressure to give 3.5 g of 2-(4-chlorophenylthiomethyl)-3-oxa-3a$\lambda^4$,4-dithia-6-chloro-1,5-diazapentalene as a yellow solid. Recrystallization from hexane gave the product a bright yellow solid metling at 97°–100° C. Elemental analysis for the product is tabulated in Table I, as Compound No. 10.

EXAMPLE 6

Preparation of 2-thiocyanatomethyl-3-oxa-3a$\lambda^4$,4-dithia-6-chloro-1,5-diazapentalene 5.0 g (0.023 mol) 2-chloromethyl-3-oxa-3a$\lambda^4$,4-dithia-6-chloro-1,5-diazapentalene and 2.0 g (0.026 mol) ammonium thiocyanate were stirred with 75 ml acetone to give a clear solution. In a few minutes, salt begin to separate. Stirring was continued for 24 hours. The salt was filtered. The acetone was removed at reduced pressure to leave solids. The solids were taken up in benzene and applied to a column of 75 g silica gel. Elution gave 3.4 g yellow solid melting at 103°–110° C. Crystallization from benzene-hexane gave bright-yellow solid melting at 109°–110° C. Elemental analysis is tabulated in Table I, as Compound No. 20.

EXAMPLE 7

Preparation of 2-cyclopropyl-3-oxa-3a$\lambda^4$,4-dithia-6-chloro-1,5-diazapentalene A slurry of 20 g (0.19 mol) cyclopropanecarboxylic acid chloride, 18.5 g (0.2 mol) aminoacetonitrile hydrochloride and 5 drops concentrated sulfuric acid in 300 ml chloroform was stirred and heated at reflux for 24 hours. The reaction was filtered and then evaporated under reduced pressure to give an oil (13.1 g), which solidified on treatment with a little hexane. Recrystallization of the solid from benzene gave N-cyanomethyl-cyclopropanecarboxamide as a white solid melting at 91°–92° C. Elemental analysis for $C_6H_8N_2O$ showed: %C, calc. 58.1, found 57.9; %H, calc. 6.5, found 6.5; %N, calc. 22.5, found 22.5.

A solution of 33 g (0.32 mol) sulfur dichloride in 25 ml dichloromethane was added dropwise to a solution of 10 g (0.08 mol) N-cyanomethylcyclopropanecarboxamide and 0.5 g tetrabutylammonium chloride in 150 ml dichloromethane. Solids began to separate during the additon. The reaction was exothermic and was maintained at about 25° C. by cooling with an ice bath. After completion of the addition and stirring for about 1.5 hours, the reaction mixture was filtered to isolate the precipitated solids. The solids were stirred with 75 ml toluene and heated at reflux until gas evolution ceased and a homogeneous solution was obtained. The toluene was evaporated under reduced pressure to leave a solid. The solid was recrystallized from hexane/benzene to give 5.5 g of 2-cyclopropyl-3-oxa-3a$\lambda^4$, 4-dithia-6-chloro-1,5-diazapentalene as a yellow solid melting at 94°–95° C. Elemental analysis for the product is tabulated in Table I as Compound No. 21.

EXAMPLE 8

Preparation of 2-trichlorovinyl-3-oxa-3a$\lambda^4$, 4-dithia-6-chloro-1,5-diazapentalene A slurry of 38.8 g (0.2 mol) trichloroacrylyl chloride and 18.5 g (0.2 mol) aminoacetonitrile hydrochloride in 150 ml chloroform was stirred and heated under reflux for 30 hours, while gases evolved and most of the hydrochloride salt dissolved. The reaction mixture was filtered while hot and the solvent evaporated under reduced pressure to give 36.1 g of N-cyanomethyl trichloroacrylamide, as an off-white solid melting at 56°–59° C. Recrystallization from benzene-hexane gave a white solid melting at 58°–60° C. Elemental analysis for $C_5H_3Cl_3N_2O$ showed: %Cl, calc. 49.8, found 50.0.

A solution of 19.2 g (0.16 mol) sulfur dichloride in 25 ml dichloromethane was added dropwise over 20 minutes at about 25° C. to a stirred solution of 10 g (0.04 mol) N-cyanomethyl trichloroacrylamide and 0.5 g tetrabutylammonium chloride in 100 ml dichloromethane. Gases were evolved during the addition. After completion of the addition and stirring for 3.5 hours, the reaction mixture was evaporated under reduced pressure to give an oil. The oil was crystallized from hexane to give 2-trichlorovinyl-3-oxa-3a$\lambda^4$, 4-dithia-6-chloro-1,5-diazapentalene as a yellow solid. Elemental analysis for the product is tabulated in Table I as compound No. 23.

EXAMPLE 9

Preparation of 2[3,5-dinitro-4-(2,4-dichlorophenoxy)phenyl]-3-oxa-3a$\lambda^4$, 4-dithia-6-chloro-1,5-diazapentalene A mixture of 7 g (0.017 mol) N-cyanomethyl-3,5-dinitro-4-(2,4-dichlorophenoxy) benzamide, 9.2 g (0.068 mol) sulfur monochloride, 0.5 g tetrabutylammonium chloride and 150 ml dichloromethane were stirred at about 25° C. After about 2 hours, gases began to evolve. After stirring a total of 20 hours, the solids (5.7 g) were separated from the reaction mixture and heated under reflux in toluene for 15 minutes. The toluene solution was treated with charcoal and filtered. The filtrate was diluted with hexane to precipitate 3.0 g of the product as an orange solid, m.p. 212°–216° C. Recrystallization from benzene-hexane gave the product as a yellow solid, m.p. 216°–218° C. Elemental analysis for $C_{15}H_5Cl_3N_4O_5S_2$ showed: %S, calc. 13.0, found 13.8; %Cl. calc. 21.6, found 19.7.

Other compounds of the invention were prepared by procedures similar to those of Examples 1–9. These compounds are reported in Table I. The structures of the compounds reported in Table I were verified by infrared spectroscopy and/or nuclear magnetic resonance analysis. The structure of Compound No. 26 was also verified by X-ray crystallographic analysis. All thiadiazinethione compounds of the invention showed a strong absorption based at about 6.1 to 6.4 microns.

FUNGICIDAL UTILITY

The compounds of the invention are useful for controlling fungi, particularly plant fungal infections caused by *Botrytis cinerea*, leaf blights caused by organisms such as *Pythrium ultimum*, *Helminthosporum sativum*, *Fusarium moniliforme*, *Rhizoctonia solani*, *Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray ot the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE A

Tomato Late Blight

Compounds of the invention were tested for the control of the Tomato Late Blight organism *Phytophthora infestans conidia.* Five- to six-week-old tomato (variety Bonny Best) seedlings were used. The tomato plants were sprayed with a 250 ppm solution of the test compound in acetone, water and a small amount of a nonionic emulsifier. The sprayed plants were then inoculated one day later with the organism, placed in an environmental chamber and incubated at 66°-68° F. and 100% relative humidity for at least 16 hours. Following the incubation, the plants were allowed to dry and then were maintained at 60-80% relative humidity for approximately 7 days. The percent disease control provided by a given test compound was based on the percent disease reduction relative to untreated check plants. The compounds giving effective control at the test concentration are tabulated in Table II.

EXAMPLE B

Tomato Early Blight

Compounds of the invention were tested for the control of the Tomato Early Blight organism, *Alternaria solani conidia.* Tomato (variety Bonny Best) seedlings of 6 to 7 weeks old were used. The tomato plans were sprayed with a 250 ppm solution of the test compound in an acetone-and-water solution containing a small amount of an non-ionic emulsifier. The sprayed plants were inoculated one day later with the organism, dried and maintained at 60-80% relative humidity for about 12 days. Percent disease control was based on the percent disease development on untreated check plants. The compounds giving effective control at the test concentration are tabulated in Table III.

EXAMPLE C

Celery Late Blight

Compounds of the invention were tested for the control of Celery Late Blight using celery (Utah) plants 11 weeks old. The Celery Late Blight organism was *Septoria apii.* The celery plants were sprayed with solutions of the candidate toxicant mixed with acetone, water and a nonionic emulsifier. The plants were then inoculated with the organism and placed in an environmental chamber and incubated at 66°-68° F. in 100% relative humidity for an extended period of time (approximately 48 hours). Following the incubation, the plants were allowed to dry and then were maintained at a 60-80% relative humidity for approximately 14 days. The percent disease control provided by a given candidate toxicant is based on the percent disease reduction relative to untreated check plants. The compounds giving effective control at the test concentrations are reported in Table IV.

EXAMPLE D

*Botrytis cinerea* control

Compounds of the invention were tested for *Botrytis cinerea* control using detached, well-developed primary leaves of a 4-6 week old horsebean plant. The leaves were dipped into a 40 ppm solution of the test compound in acetone and water containing a small amount of a nonionic emulsifier, then taken out and placed in a petri plate lined with two pieces of filter paper. The leaves were allowed to dry while the filter paper was kept moist by adding water as required. The treated leaves were then inoculated with the spores of *Botrytis cinerea* fungus grown on potato. The plate was covered after inoculation and kept at 23.5° C. The filter-paper lining of the plate was kept saturated with water throughout the test. The rate of disease incidence was determined in 3 to 5 days, when the disease symptoms were fully evident on non-treated check leaves. The percentage disease control provided by the test compound was calculated as the percentage disease reduction based on the non-treated check leaves. The effectiveness of the compounds tested for fungicidal activity is reported in Table V in terms of micrograms/$cm^2$ for 99% control of the fungus.

EXAMPLE E

Powdery Mildew

The powdery mildew test was made using bean seedlings (var. Bountiful) with well-developed primary leaves. The pathogen was *Erysiphe polygoni.* The bean seedlings were sprayed with a 250 ppm solution of the test compound in an acetone-water mixture containing a nonionic emulsifier. The treated plants were inoculated one day after spray application of the test compound with the pathogen. The plants were then maintained in a greenhouse at 60-80% relative humidity and at a temperature of 68°-70° F. The rate of infection on the leaves was made after about 10 days. The percent disease control provided by a given test compound was based on the disease reduction relative to untreated check plants. The compounds of the invention giving effective control at the test concentrations are reported in Table VI.

EXAMPLE F

Mycelia Inhibition

The compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were innoculated with the particular mycelium growth by covering the paper with a potato dextrose broth culture of mycelial suspension. The inoculated papers were then placed on potato dextrose agar plates and sprayed by means of a microsprayer with the fungicidal solution. The treated paper strips were incubated at 25° C. and data are taken after 24 hours. Fungicidal activities are measured by a zone of inhibited mycelial growth from the center of the paper strip. The effectiveness of the compounds tested for fungicidal activity is reported in Table VII in terms of micrograms/cm$^2$ for 99% control of the fungus.

HERBICIDAL UTILITY

The compounds of the present invention wherein R is aryloxymethyl are also herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foilage and other plant parts. Generally, the herbicidal compounds of the invention are most effective against broadleaved weeds.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite and montmorillonite. In addition, talcs, pyrophillite, diatomaceous silica, synthetic fine silicas, calcium alumino-silicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

Pre-emergent herbicidal tests on representative compounds of the invention were made using the following method:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 micrograms/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table VIII.

TABLE I

Compound of the formula

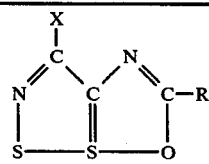

| Compound No. | R | Melting Point, °C. | Sulfur Calc. | Sulfur Found | Chlorine Calc. | Chlorine Found |
|---|---|---|---|---|---|---|
| 1 | 3,4-(Cl)$_2$-φ | 170–172 | 19.7 | 20.3 | 32.7 | 31.1 |
| 2 | 2-F-φ | 177–178 | 23.3 | 23.5 | 12.9 | 13.8 |
| 3 | 4-Cl-φ | 156–157 | 22.0 | 22.8 | 24.3 | 21.9 |
| 4 | 3-CF$_3$-φ | 160–161 | 19.8 | 20.0 | 10.9 | 11.2 |
| 5 | ClCH$_2$ | 122–124 | 28.0 | 27.2 | 31.0 | 30.5 |
| 6 | φ | 158–160 | 25.0 | 23.4 | 13.8 | 14.4 |
| 7 | 4-NO$_2$-φ | 166–167 | 21.2 | 19.5 | 11.7 | 10.8 |
| 8 | 2-furyl | 126–133 | 26.0 | 26.1 | 14.4 | 13.9 |
| 9 | ICH$_2$ | 107–108 | 20.0 | 21.2 | 11.0 | 10.9 |
| 10 | 4-Cl-φ-SCH$_2$ | 97–100 | 28.5 | 28.6 | 21.0 | 21.6 |
| 11 | 4-Cl-φ-CH$_2$SCH$_2$ | 110–111 | 27.4 | 27.8 | 20.2 | 19.7 |
| 12 | 2-thienyl | 131–134 | 36.6 | 36.7 | 13.5 | 15.1 |
| 13 | 2-OH-φ | 150–165 | 23.5 | 22.6 | 13.0 | 12.1 |

TABLE I-continued

Compound of the formula:

$$\begin{array}{c} X \\ \| \\ C \\ N \diagup \diagdown N \\ | \quad C \quad \| \\ N \quad \| \quad C-R \\ \diagdown \quad C \quad \diagup \\ S \quad \diagdown \quad O \\ \quad S \end{array}$$

| Compound No. | R | Melting Point, °C. | Sulfur Calc. | Sulfur Found | Chlorine Calc. | Chlorine Found |
|---|---|---|---|---|---|---|
| 14 | Cl$_3$C | 99–100 | 21.5 | 22.0 | 47.5 | 46.5 |
| 15 | 2,6-(Cl)$_2$-φ | 188–190 | 19.4 | 20.0 | 32.2 | 32.6 |
| 16 | 3,5-(Cl)$_2$-φ | 186–187 | 19.4 | 20.1 | 32.2 | 31.3 |
| 17 | 2-NO$_2$-5-Cl-φ | 167 | 19.0 | 18.1 | 21.1 | 20.5 |
| 18 | CH$_2$CH(Cl)$_2$-φ | 90–91 | 23.1 | 25.9 | 38.3 | 37.5 |
| 19 | 2-CH$_3$-4-Cl-φ-O—CH$_2$ | 131–133 | 19.1 | 19.2 | 21.2 | 21.2 |
| 20 | NCS—CH$_2$-φ | 109–110 | 38.2 | 38.9 | 14.1 | 13.9 |
| 21 | Cyclopropyl | 94–95 | 29.0 | 29.6 | 16.1 | 16.2 |
| 22 | 3-SCN-φ | 168–169 | 30.7 | 30.0 | 11.3 | 9.8 |
| 23 | Cl$_2$C=CCl | 108–109 | 20.7 | 20.9 | 45.7 | 44.2 |
| 24 | CH$_3$CHI— | 78–79 | 19.1 | 20.0 | 10.6 | 11.3 |
| 25 | 4-Cl-φ-O—CH$_2$ | 181–182 | 20.0 | 19.2 | 22.1 | 20.8 |
| 26 | CH$_3$CHCl | 61–64 | 26.4 | 26.4 | 29.2 | 29.2 |
| 27 | 2,5-Cl$_2$—φOCH$_2$— | 164–165 | 18.0 | 18.0 | 30.0 | 28.2 |
| 28 | 2-I-φ | 176 | 16.8 | 16.6 | 9.3 | 10.3 |
| 29 | 2,4-Cl$_2$—φOCH$_2$— | 150–151 | 18.0 | 18.0 | 30.0 | 28.1 |
| 30 | CH$_3$CO$_2$CH(CH$_3$)Oφ— | 118–122 | 17.9 | 16.1 | 9.9 | 10.1 |

φ = phenyl phenyl

Table II

| Compound No. | Tomato Late Blight % Control |
|---|---|
| 1 | 60 |
| 2 | 93 |
| 3 | 98 |
| 4 | 35 |
| 5 | 81 |
| 6 | 93 |
| 7 | 90 |
| 9 | 62 |
| 10 | 81 |
| 11 | 93 |
| 12 | 89 |
| 13 | 27 |
| 17 | 80 |
| 18 | 89 |
| 21 | 97 |
| 23 | 98 |
| 24 | 23 |
| 28 | 75 |
| 29 | 88 |

TABLE III

| Compound No. | Tomato Early blight % Control |
|---|---|
| 1 | 39 |
| 5 | 73 |
| 6 | 75 |
| 7 | 23 |
| 8 | 56 |
| 9 | 81 |
| 12 | 68 |
| 13 | 51 |
| 14 | 21 |
| 21 | 23 |
| 24 | 71 |
| 25 | 88 |
| 29 | 69 |

TABLE IV

| Compound No. | Celery Late Blight % Control |
|---|---|
| 3 | 68 |
| 4 | 23 |
| 9 | 71 |
| 19 | 92 |

Table V

| Compound No. | Botrytis Cinerea |
|---|---|
| 2 | 1.6 |
| 3 | 1.1 |
| 8 | 0.15 |
| 9 | 0.37 |
| 12 | 1.4 |
| 15 | 1.6 |
| 18 | 0.82 |
| 20 | 0.88 |

TABLE VI

| Compound No. | Powdery Mildew % Control |
|---|---|
| 2 | 35 |
| 3 | 76 |
| 4 | 80 |
| 6 | 100 |
| 12 | 54 |
| 16 | 23 |
| 19 | 57 |
| 22 | 35 |
| 23 | 95 |
| 25 | 29 |
| 28 | 69 |
| 29 | 37 |

TABLE VII

| Compound No. | Pythium ultimum | Rhizoctonia solani | Aspergillus niger | Fusarium moniliforme |
|---|---|---|---|---|
| 4 | >1.7 | 0.65 | >1.7 | >1.7 |
| 5 | 0.12 | 0.38 | 1.1 | >1.7 |
| 8 | 0.29 | 0.34 | 0.49 | 0.95 |
| 9 | 0.12 | 0.6 | 0.52 | 0.82 |
| 10 | >1.7 | 1.2 | 0.52 | >1.7 |
| 11 | >1.7 | 0.5 | 0.46 | >1.7 |
| 12 | >1.7 | 0.5 | 1.2 | >1.7 |

TABLE VII-continued

| Compound No. | Pythium ultimum | Rhizoctonia solani | Aspergillus niger | Fusarium moniliforme |
|---|---|---|---|---|
| 13 | >1.7 | 0.5 | 0.98 | >1.7 |
| 20 | — | 0.33 | 0.6 | >1.7 |

TABLE VIII

| Compound No. | Herbicidal Effectiveness - Pre/Post | | | | | |
|---|---|---|---|---|---|---|
| | O | W | C | M | P | L |
| 19 | 35/10 | 75/40 | 85/0 | 100/100 | 100/100 | 100/95 |
| 25 | 0/0 | 20/0 | 70/0 | 95/85 | 90/85 | 90/85 |
| 27 | 0/0 | 55/0 | 55/90 | 87/80 | 80/75 | 82/90 |
| 29 | 0/20 | 95/20 | 97/20 | 100/100 | 100/100 | 100/97 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avena fatua*)

What is claimed is:

1. A compound of the formula

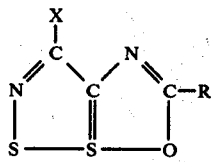

wherein X is chloro or bromo and R is alkyl of 1 to 6 carbon atoms; haloalkyl of 1 to 6 carbon atoms and of 1 to 3 of the same or different halogen selected from fluoro, chloro, bromo or iodo; halovinyl of 1 to 3 of the same or different halogens selected from fluoro, chloro, bromo or iodo; cycloalkyl of 3 to 6 carbon atoms; thiocyanatoalkyl of 1 to 3 carbon atoms; phenyl or phenoxy substituted with up to 3 of the same or different substituents selected from hydroxy, fluoro, chloro, bromo, iodo, trifluoromethyl, trichloromethyl, tribromomethyl, alkyl of 1 to 4 carbon atoms, alkoxy of 1 to 4 carbon atoms, alkoxycarbonylalkoxy of 3 to 6 carbon atoms, nitro, cyano, thiocyanato or isothiocyanato; phenoxymethyl or phenylthiomethyl wherein the phenyl ring is substituted with up to 3 of the same or different substituents selected from fluoro, chloro, bromo, iodo or alkyl of 1 to 4 carbon atoms; benzyloxymethyl or benzylthiomethyl wherein the benzyl ring is substituted with up to 2 of the same or different substituents selected from fluoro, chloro, bromo, iodo, or alkyl of 1 to 4 carbon atoms; furyl; or thienyl.

2. The compound of claim 1 wherein X is chloro.

3. The compound of claim 2 wherein R is haloalkyl of 1 to 3 carbon atoms and 1 to 3 of the same or different substituents selected from fluoro, chloro, bromo or iodo.

4. The compound of claim 3 wherein R is monohalomethyl wherein the halo is chloro, bromo or iodo.

5. The compound of claim 2 wherein R is phenyl substituted with up to 2 of the same or different substituents selected from hydroxy, fluoro, chloro, bromo, nitro, alkyl of 1 to 4 carbon atoms, trifluoromethyl or trichloromethyl.

6. The compound of claim 2 wherein R is phenoxymethyl, phenylthiomethyl, benzyloxymethyl or benzylthiomethyl wherein the aromatic ring is substituted with up to 2 of the same or different substituents selected from fluoro, chloro, bromo, iodo or alkyl of 1 to 4 carbon atoms.

7. A process for preparing the compound of claim 1 which comprises contacting a sulfur halide selected from the group consisting of sulfur chloride and sulfur bromide with a carboxamide having the formula

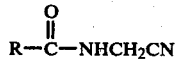

wherein R is as defined in claim 1, in the liquid phase, using a relative mol ratio of at least about 2 mols of said sulfur halide per mol of said carboxamide, under reactive conditions thereby yielding the corresponding compound of claim 1.

8. The process of claim 7 wherein the molar ratio of carboxamide to sulfur halide varies from about 1:2 to 1:5.

9. The process of claim 8 wherein the sulfur halide is sulfur dichloride.

10. The process of claim 8 wherein the sulfur halide is sulfur monochloride.

* * * * *

UNITED STATES PATENT AND TRADEMARK OFFICE
CERTIFICATE OF CORRECTION

PATENT NO. : 4,179,441
DATED : December 18, 1979
INVENTOR(S) : Joseph E. Moore

It is certified that error appears in the above-identified patent and that said Letters Patent are hereby corrected as shown below:

Col. 3, line 25, "guaternary" should read --quaternary--.
Col. 5, line 2, "250°C" should read --25°C--.
Col. 6, line 34, "begin" should read --began--.
Col. 13, Table I, Compound 18, "$CH_2CH...$" should read --$CH_3CH...$--.
Col. 13, Table I, footnote, "φ=phenyl phenyl" should read --φ=phenyl--.
Col. 13, Table I, under heading Melting Point, °C, Compound 28, "176" should read --175-176--.

Signed and Sealed this

First Day of April 1980

[SEAL]

Attest:

SIDNEY A. DIAMOND

Attesting Officer

Commissioner of Patents and Trademarks